US011937790B2

(12) United States Patent
Hegenberger (10) Patent No.: US 11,937,790 B2
(45) Date of Patent: *Mar. 26, 2024

(54) VAGINAL SPECULUM (71) Applicant: HEGENBERGERSPECULUM ApS, Karrebæksminde (DK)

(72) Inventor: Malene Kruse Hegenberger, Karrebaeksminde (DK)

(73) Assignee: HEGENBERGERSPECULUM APS, Karrebæksminde (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/875,578

(22) Filed: May 15, 2020

(65) Prior Publication Data
US 2020/0275832 A1 Sep. 3, 2020

Related U.S. Application Data

(63) Continuation of application No. 16/539,735, filed on Aug. 13, 2019, now Pat. No. 10,694,935, which is a (Continued)

(30) Foreign Application Priority Data

Nov. 10, 2017 (EP) .................................. 17200995
Jun. 7, 2018 (EP) .................................. 18176417

(51) Int. Cl.
*A61B 1/32* (2006.01)
*A61B 1/00* (2006.01)
(Continued)

(52) U.S. Cl.
CPC .............. *A61B 1/32* (2013.01); *A61B 1/0008* (2013.01); *A61B 17/0218* (2013.01);
(Continued)

(58) Field of Classification Search
CPC .. A61B 1/32; A61B 1/303; A61B 1/31; A61B 1/24; A61B 17/0218; A61B 17/42;
(Continued)

(56) References Cited

U.S. PATENT DOCUMENTS 3,030,947 A 4/1962 Engelbert
3,745,992 A 7/1973 Poirier
(Continued)

FOREIGN PATENT DOCUMENTS

CN 201 337 440 11/2009
CN 101 889 856 11/2010
(Continued)

OTHER PUBLICATIONS

International Search Report and Written Opinion for corresponding international application No. PCT/EP2018/080842, 14 pgs., dated Jan. 28, 2019.
(Continued)

*Primary Examiner* — Tracy L Kamikawa
(74) *Attorney, Agent, or Firm* — Crowell & Moring LLP (57) ABSTRACT

A vaginal speculum may include a vaginal assembly with at least two longitudinal separating elements connected at a distal end for insertion into the vagina of a subject. The vaginal speculum is configured for holding the vaginal walls of the subject apart, thereby permitting examination and/or suturing of at least the posterior part of the vaginal tissue. A set of vaginal specula may be provided in predefined sizes such that the specula suitably fit a range of anatomies. A method is described for providing an unobstructed view of at least the posterior part of the vaginal wall during suturing of a subject after the subject has given birth.

17 Claims, 7 Drawing Sheets

Related U.S. Application Data continuation of application No. PCT/EP2018/080842, filed on Nov. 9, 2018.

(51) Int. Cl.
   *A61B 17/02* (2006.01)
   *A61B 17/42* (2006.01)
   *A61B 17/00* (2006.01)

(52) U.S. Cl.
   CPC .... *A61B 17/42* (2013.01); *A61B 2017/00862* (2013.01); *A61B 2217/005* (2013.01)

(58) Field of Classification Search
   CPC ...... A61B 17/0206; A61B 2017/00862; A61B 90/02; A63B 21/02; A63B 23/20; A61F 2/005
   See application file for complete search history.

(56) References Cited

U.S. PATENT DOCUMENTS

| | | | |
|---|---|---|---|
| 4,632,093 A | 12/1986 | Giomi | |
| 4,638,792 A | 1/1987 | Burgin | |
| 4,966,130 A | 10/1990 | Montaldi | |
| 5,018,507 A * | 5/1991 | Montaldi | A61B 1/32 600/222 |
| 6,460,542 B1 * | 10/2002 | James | A61F 2/005 128/885 |
| 6,676,594 B1 * | 1/2004 | Zunker | A61F 2/005 600/29 |
| 6,752,749 B2 * | 6/2004 | Stein | A63B 23/20 482/121 |
| 7,607,917 B2 | 10/2009 | Vimicchi | |
| 10,694,935 B2 * | 6/2020 | Hegenberger | A61B 1/303 |
| 2006/0135853 A1 | 6/2006 | Chin | |
| 2009/0081611 A1 | 3/2009 | Hines | |
| 2010/0016674 A1 * | 1/2010 | Mills | A61B 1/32 600/207 |
| 2010/0041954 A1 | 2/2010 | Bastia | |
| 2011/0034776 A1 | 2/2011 | Dixon et al. | |
| 2012/0053535 A1 | 3/2012 | Blurton et al. | |
| 2012/0083658 A1 | 4/2012 | Hahn et al. | |
| 2012/0136199 A1 * | 5/2012 | Hou | A61F 2/005 600/29 |
| 2013/0053863 A1 | 2/2013 | Juravic | |
| 2013/0253376 A1 | 9/2013 | Juravic et al. | |
| 2014/0303447 A1 * | 10/2014 | Singh | A61B 46/30 600/207 |
| 2018/0014721 A1 | 1/2018 | Rullo | |
| 2018/0344144 A1 | 12/2018 | Bouquet | |
| 2019/0000353 A1 | 1/2019 | Carty | |
| 2019/0167464 A1 | 6/2019 | Lovato | |

FOREIGN PATENT DOCUMENTS

| | | |
|---|---|---|
| CN | 103415242 A | 11/2013 |
| SU | 992017 A1 | 2/1983 |
| WO | WO 1996/012437 A1 | 5/1996 |
| WO | WO 2012/047725 | 4/2012 |
| WO | WO 2015/031282 A1 | 3/2015 |
| WO | WO2017/181218 A1 | 10/2017 |

OTHER PUBLICATIONS

Chinese Office Action with English translation of the main points regarding 201880076266.0 dated Jan. 19, 2023.

* cited by examiner

VAGINAL SPECULUM

CROSS-REFERENCE TO RELATED APPLICATIONS

This application claims priority as a Continuation of application Ser. No. 16/539,735 filed on Aug. 13, 2019, now U.S. Pat. No. 10,694,935, which claims priority as a Continuation of PCT application serial number PCT/EP2018/080842, filed Nov. 9, 2018, which claims priority to European patent application serial numbers 17200995.3 filed Nov. 10, 2017 and 18176417.6 filed Jun. 7, 2018, each which is incorporated by reference herein in its entirety.

DEVICE

The present invention relates to a vaginal speculum permitting examination and/or suturing of at least the posterior part of the vaginal tissue.

The vaginal speculum of the invention is of a design that is ergonomic for the patient and the user, providing an unobstructed view of the vaginal tissue and access for examination, suturing, surgery or training purposes.

BACKGROUND OF INVENTION

An instrument known as a speculum is frequently used to dilate or enlarge cavities in the human body for medical examination or operation. Specula for vaginal examination purposes generally comprise parts that are inserted into the vagina to spread and dilate the vaginal walls, connected at a base or handle with a locking mechanism, and may include lights, suction devices, comfortable padding, absorbent material or other attachments as necessary for the specific task, and may be coated with a lubricating gel or anesthetic.

For applications such as postpartum suturing procedures, where the operator has to have a clear view of and access to the vaginal walls in order to effectively perform suturing, the devices used entail hooks or traction mechanisms to dilate and pull the vaginal walls into position. Where this is not practicable, the operator will use the fingers of one or both hands to dilate the vaginal for examination and then hold one or more fingers of one hand in place as a guide for suturing while unable to see the actual suturing location. The fingers of one or both hands are then used again to dilate the vagina to inspect the suturing result. When training students, the trainer may use their fingers to dilate the vagina while the student performs suturing, requiring both student and trainer to assume constrained postures for extended periods. This use of potentially painful or damaging hooks or traction devices, poor or no visibility of the operating area, and constrained postures and hand positions often result in a protracted and difficult procedure for both the patient and the operator or student and trainer. This has a corresponding effect on the suturing results, sometimes necessitating resuturing.

Due to the abovementioned difficulties associated with examination or operation of the vagina, it is an object of the present invention to provide an improved vaginal speculum that provides a clearer, less obstructed view of the area to be examined, sutured or operated on that facilitates the suturing process, and which is furthermore easier to handle. It is further an object of the present invention to provide a vaginal speculum that facilitates examination or operation without the additional use of hooks or of the fingers of the operator or trainer. It is further an object of the present invention to provide a vaginal speculum that retains the anterior vaginal wall, thereby supporting the bladder, to permit an unobstructed view and access for examination, suturing or operation.

SUMMARY OF INVENTION

The present disclosure provides a vaginal speculum that provides a clearer, less obstructed view of the area to be examined, sutured or operated on, and which further facilitates examination or operation without the additional use of hooks or of the fingers of the operator or trainer. For example, the vaginal speculum may be configured to retain the anterior vaginal wall, thereby supporting the bladder, to permit an unobstructed view and access for examination, suturing or operation. The present disclosure further provides a vaginal speculum which may facilitate the suturing process, such as a vaginal speculum that facilitates handling of suture materials. The present disclosure further provides a vaginal speculum, which is easier and simpler to insert and remove.

In a first aspect the present disclosure relates to a vaginal speculum comprising a vaginal assembly comprising at least two longitudinal separating elements connected at a distal end for insertion into the vagina of a subject. The vaginal speculum is preferably configured for holding the vaginal walls of the subject apart, thereby permitting examination and/or suturing of at least the posterior part of the vaginal tissue. It should be understood that references to the proximal and distal end of the assembly are made from the doctor's, surgeon's or other user's point of view. This means that the distal end refers to the end of the vaginal assembly inserted into the vagina first.

In a preferred embodiment, the vaginal speculum according to the first aspect is configured such that the speculum assumes the desired shape on insertion.

A second aspect of the present invention relates to a set of vaginal specula comprising a number of specula according to the first aspect of the invention, wherein said specula are provided in predefined sizes such that the specula suitably fit a range of anatomies.

A third aspect of the invention relates to a method for providing an unobstructed view of at least the posterior part of the vaginal wall during suturing of a subject after said subject has given birth. The method comprising the steps of 1) inserting a longitudinal vaginal assembly from a vaginal speculum into the vagina of the subject, and 2) engaging a locking element with the vaginal assembly such that the vaginal assembly creates a transverse separation force to separate and hold apart the vaginal walls of the subject while providing an unobstructed view of at least the posterior part of the vaginal wall for examination and/or suturing of said subject.

Advantageously, the vaginal speculum according to the first aspect may be used in the method according to the third aspect. Thus, in a preferred embodiment the vaginal speculum is configured such the speculum assumes the desired shape on insertion.

A fourth aspect of the invention relates to a method for providing an unobstructed view of at least the posterior part of the vaginal wall during suturing of a subject after said subject has given birth. The method comprising the steps of 1) inserting a longitudinal vaginal assembly from a vaginal speculum into the vagina of the subject, such that the vaginal assembly creates a transverse separation force to separate and hold apart the vaginal walls of the subject while providing an unobstructed view of at least the posterior part of the vaginal wall for examination and/or suturing of said subject.

According to the present invention there is provided a vaginal speculum comprising:
- a vaginal assembly comprising at least two longitudinal separating elements connected at a distal end for insertion into the vagina of a subject,
- wherein the vaginal speculum is configured for holding the vaginal walls of the subject apart, thereby permitting examination and/or suturing of at least the posterior part of the vaginal tissue.

Preferably, the vaginal speculum further comprises a locking element configured for engagement with the vaginal assembly for creating a transverse separation force at a proximal end of the separating elements for holding the vaginal walls of the subject apart.

Advantageously the locking element is an integral part of the vaginal assembly.

Conveniently, the locking element is configured for detachable engagement with the vaginal assembly.

Preferably, the vaginal assembly and locking element are shaped such that at least the posterior part of the vaginal tissue is exposed for examination and/or suturing when the vaginal assembly is inserted into the vagina and the locking element is engaged with the vaginal assembly.

Advantageously, the locking element is shaped as an arch or an inverted V.

Conveniently, the locking element is predominantly elastic in one or more predefined parts.

Preferably, the speculum is configured for at least partially exposing a lateral wall of the vagina.

Advantageously, the lateral wall of the vagina is at least partially exposed by using the speculum in a rotated orientation.

Conveniently, the speculum is for use during vaginal suturing after the subject has given birth.

Preferably, the vaginal assembly further comprises proximal base elements configured to rest on the skin outside the vagina after the vaginal assembly has been inserted into the vagina.

Advantageously, the proximal base elements are flattened and curve outwards from the separating elements such that they can rest on the skin outside the vagina after the vaginal assembly has been inserted into the vagina.

Conveniently, the proximal base elements are flattened and extending transversely such that they can rest on the skin outside the vagina after the vaginal assembly has been inserted into the vagina.

Preferably, the proximal base elements are located at the proximal ends of the separating elements.

Advantageously, the proximal base elements are configured for resting against, separating and holding apart the labia majora and labia minora.

Conveniently, the vaginal speculum further comprises soft padding material attachable or permanently attached to at least part of the surfaces of the speculum.

Preferably, the padding material is located at the proximal base elements.

Advantageously, the padding material is located at the separating elements.

Conveniently, the vaginal speculum further comprises an absorbent material attachable or permanently attached to at least part the surfaces of the speculum.

Preferably, the absorbent material is attached or attachable to the inside of the separating elements.

Advantageously, the vaginal assembly comprises proximal engagement sections configured for engagement with the locking element.

Conveniently, the engagement sections are located at the base elements.

Preferably, the vaginal speculum is configured such that the transverse separation force is adjustable.

Advantageously, the vaginal speculum comprises a plurality of engagement sections such that the transverse separation force created by the locking element may be adjusted by engagement with different engagement sections.

Conveniently, the vaginal speculum comprises a plurality of locking elements with different elastic properties such that the transverse separation force is adjustable by using different locking elements.

Preferably, the transverse separation force is adjustable by a screw mechanism.

Advantageously, the vaginal assembly is configured for supporting the anterior vaginal wall after insertion into the vagina.

Conveniently, the vaginal assembly further comprises an anterior vaginal wall element configured for supporting the anterior vaginal wall.

Preferably, the anterior vaginal wall element is connected at the distal end of the vaginal assembly, extending in the proximal direction from the distal end, preferably in the shape of a tongue such as a flattened and rounded shape.

Advantageously, the anterior vaginal wall element is made from an elastic material such that it is configured to support the anterior vaginal wall.

Conveniently, the anterior vaginal wall element comprises a depression adapted to be grasped by the user on insertion and removal.

Preferably, the anterior vaginal wall element comprises a surface profile adapted to be grasped by the user on insertion and removal.

Conveniently, the vaginal assembly is configured for supporting the pressure exerted by the bladder on the anterior vaginal wall of the subject.

Preferably the proximal ends of the separating elements comprises a surface profile adapted to be grasped by the user on insertion and removal.

Advantageously, at least one of the proximal ends of the separating elements comprises one or more projections for holding materials for examination or suturing.

Conveniently, at least one of the proximal ends of the separating elements comprises one or more slits for securing suture materials.

Preferably, the vaginal speculum is fabricated at least partially from an elastic material.

Advantageously, the vaginal speculum is fabricated entirely from an elastic material.

Conveniently, the vaginal speculum is fabricated from metal or nylon or a plastic material such as polyethylene (PE), polypropylene (PP), polystyrene (PS) and polyvinyl chloride (PVC).

Preferably, at least part of the surface of the vaginal assembly is coated by a different material than the material of the vaginal assembly.

Advantageously, at least part of the surface of the vaginal assembly is coated with a fluid or gel before or after packaging and before insertion into the vagina.

Conveniently, the vaginal speculum is fabricated using injection molding or additive manufacturing.

Preferably, the vaginal assembly or the entire speculum is disposable.

Advantageously, the speculum is sterilized and in a sealed package prior to use.

Conveniently, the vaginal speculum is configured to be resiliently elastic such that the vaginal assembly can be transversely compressed for insertion into the vagina.

Preferably, the vaginal assembly is packaged in a compressed and compact condition for insertion into the vagina.

Advantageously, the vaginal speculum is configured for attachment of additional equipment, such as one or more lights, or one or more cameras, or one or more suction tubes.

Conveniently, the vaginal speculum further comprises one or more permanent or removable pads such as soft padding and/or fluid absorbent padding.

According to a further aspect of the invention, there is provided a set of vaginal specula comprising a number of specula according as defined above, wherein said specula are provided in predefined sizes such that the specula suitably fit a range of anatomies.

According to another aspect of the invention, there is provided a method for providing an unobstructed view of at least the posterior part of the vaginal wall during examination and/or suturing of a subject after said subject has given birth, the method comprising the steps of:
 inserting a longitudinal vaginal assembly from a vaginal speculum into the vagina of the subject, and
 engaging a locking element with the vaginal assembly such that the vaginal assembly creates a transverse separation force to separate and hold apart the vaginal walls of the subject while providing an unobstructed view of at least the posterior part of the vaginal wall for examination and/or suturing of said subject.

Preferably, the method further comprises the step of transversely compressing the vaginal assembly prior to insertion into the vagina.

Advantageously, the method further comprises the step of releasing the vaginal assembly from a compressed and compact configuration after insertion into the vagina.

Conveniently, the vaginal assembly and locking element used in the method are the vaginal assembly and locking element according as defined above.

According to another aspect of the invention, there is provided a method for providing an unobstructed view of at least the posterior part of the vaginal wall during examination and/or suturing of a subject after said subject has given birth, the method comprising the steps of:
 inserting a longitudinal vaginal assembly from a vaginal speculum into the vagina of a subject, such that the vaginal assembly creates a transverse separation force to separate and hold apart the vaginal walls of the subject while providing an unobstructed view of at least the posterior part of the vaginal wall for examination and/or suturing of said subject.

Preferably, the vaginal speculum used in the method outlined in the preceding paragraph is a speculum as herein defined.

According to a further aspect of the invention, there is provided a kit-of-parts comprising a vaginal speculum as described above in the form of a sterile, pre-packaged kit-of-parts for single use.

According to another aspect of the invention, there is provided a method for inserting a vaginal speculum into the vagina of a subject, wherein the method comprises the steps of providing a vaginal speculum as described above and inserting the distal end of the speculum into the vagina of the subject.

Preferably, prior to insertion the longitudinal separating elements are transversely compressed towards each other from a resting state to a compressed state.

Advantageously, after insertion the separating elements are released and return from the compressed state to the resting state.

According to a further aspect of the invention, there is provided a method of suturing vaginal tissue comprising the steps of:
 inserting a vaginal speculum as described above into the vagina of a subject using the method as described above; and
 suturing a tear in the vaginal tissue of the subject.

According to another aspect of the invention, there is provided a method of manufacturing a vaginal speculum as described above via injection molding or additive manufacturing.

Definitions

Anterior vaginal wall: front wall of the vagina, behind which is located the bladder and urethra of the subject.

Posterior vaginal wall: rearward wall of the vagina, behind which is located the rectum and anus.

Lateral vaginal walls: vaginal walls connecting the anterior and posterior walls of the vagina on each side.

Distal end: defines the end of the vaginal speculum farther away from the medical practitioner when in use. In other words, it is the end of the speculum which is first inserted into the vagina of the subject when in use.

Proximal end: the proximal end defines a part of the speculum which is accessible to the medical practitioner when in use.

BRIEF DESCRIPTION OF DRAWINGS

The embodiments of the invention, together with its advantages, may be best understood from the following detailed description taken in conjunction with the accompanying figures.

DETAILED DESCRIPTION OF THE INVENTION

The first aspect of the present disclosure relates to a vaginal speculum permitting examination and/or suturing of at least the posterior part of the vagina. Preferably the vaginal speculum provides a clear and unobstructed view of at least the posterior part of the vagina. In one embodiment of the present invention, the vaginal assembly is configured for exerting sufficient force on the vaginal walls for holding the walls apart and exposing at least the posterior part of the vagina. Advantageously, the vaginal assembly is configured to assume the desired shape on insertion. This may be obtained by tailoring the materials and dimensions of the assembly such that sufficient strength, elasticity, and resilience are acquired. In another embodiment the vaginal speculum further comprises a locking element configured for engagement with the vaginal assembly for creating a transverse separation force at a proximal end of the separating elements for holding the vaginal walls of the subject apart. This locking element may be an integral part of the vaginal assembly or it may be configured for detachable engagement with the vaginal assembly.

In one embodiment the vaginal assembly and locking element are shaped such that at least the posterior part of the vaginal tissue is exposed for examination and/or suturing when the vaginal assembly is inserted into the vagina and the locking element is engaged with the vaginal assembly. The locking element should therefore be shaped such that it does not obstruct the view and/or access to at least the posterior area of the vagina. This may be accomplished by a large variety of shapes for the locking element. In one embodiment the locking element is shaped as an arch or an inverted V. This shape for the locking element may be preferred such that it does not extend in a direct transverse line between the separating elements, which could obstruct the view and or access to the posterior part of the vagina.

The locking element is preferably constructed such that it can exert a force on the vaginal assembly for separating the vaginal walls. In one embodiment the locking element is predominantly elastic in one or more predefined parts. Here, elastic is understood as being capable of returning to its original length, shape or configuration after being deformed, where deformation may refer to stretching, compression or expansion. An elastic material may be able to return or recover its original shape and size spontaneously after deformation. Elastic may further refer to materials exerting a force on its surroundings when deformed, as the material seeks to return to its original shape.

The speculum may also be configured for at least partially exposing a lateral wall of the vagina. This is achieved e.g. by using the speculum in a rotated orientation. The present invention may be used for various types of examinations or for suturing or surgery. In one embodiment the speculum is for use during vaginal suturing after the subject has given birth.

The vaginal assembly may further comprise proximal base elements configured to rest on the skin outside the vagina after the vaginal assembly has been inserted into the vagina. One purpose of the base elements is that they may provide better comfort for the subject when the vaginal speculum is inserted into the vagina and to provide better protection of the sensitive tissue of the subject when in contact with the vaginal speculum. The proximal base elements are in one embodiment flattened and curve outwards from the separating elements such that they can rest on the skin outside the vagina after the vaginal assembly has been inserted into the vagina. In another embodiment the proximal base elements are flattened and extending transversely such that they can rest on the skin outside the vagina after the vaginal assembly has been inserted into the vagina. The proximal base elements are preferably located at the proximal ends of the separating elements. Furthermore, the proximal base elements are preferably configured for resting against, separating and holding apart the labia majora and labia minora.

In one embodiment of the present invention the vaginal assembly comprises proximal engagement sections configured for engagement with the locking element. The base elements may also be used for this purpose. Therefore, in another embodiment the engagement sections are located at the base elements. The vaginal speculum may also be configured such that the transverse separation force is adjustable. In one embodiment the vaginal speculum comprises a plurality of engagement sections such that the transverse separation force created by the locking element may be adjusted by engagement with different engagement sections. In another embodiment the transverse separation force is adjustable by a screw mechanism. The vaginal speculum may also comprise a plurality of locking elements with different elastic properties such that the transverse separation force is adjustable by using different locking elements. In this manner, some locking elements are configured such that they exert a larger force on the surroundings, such as the vaginal assembly when engaged with the vaginal assembly, than other locking elements.

In some embodiments the vaginal assembly is furthermore configured for supporting the anterior vaginal wall after insertion into the vagina. The vaginal assembly may therefore further comprise an anterior vaginal wall element configured for supporting the anterior vaginal wall. In one embodiment the anterior vaginal wall element is connected at the distal end of the vaginal assembly, extending in the proximal direction from the distal end, and preferably in the shape of a tongue such as a flattened and rounded shape. The anterior vaginal wall element may be made from an elastic material such that it is configured to support the anterior vaginal wall. The anterior vaginal wall element may thereby at least temporarily deform when inserted into the vagina such that it exerts a force on the anterior vaginal wall of the subject. In another embodiment the vaginal assembly is configured for supporting the pressure exerted by the bladder on the anterior vaginal wall of the subject.

To facilitate easy and safe insertion and removal of the vaginal assembly, the vaginal assembly advantageously comprises one or more areas adapted to be grasped with one or more fingers. Further advantageously, the areas may be grasped simultaneously with two or more fingers from a single hand, such that the assembly is simple and easy to handle, and further simple and easy to compress with respect to insertion.

Figure 11:
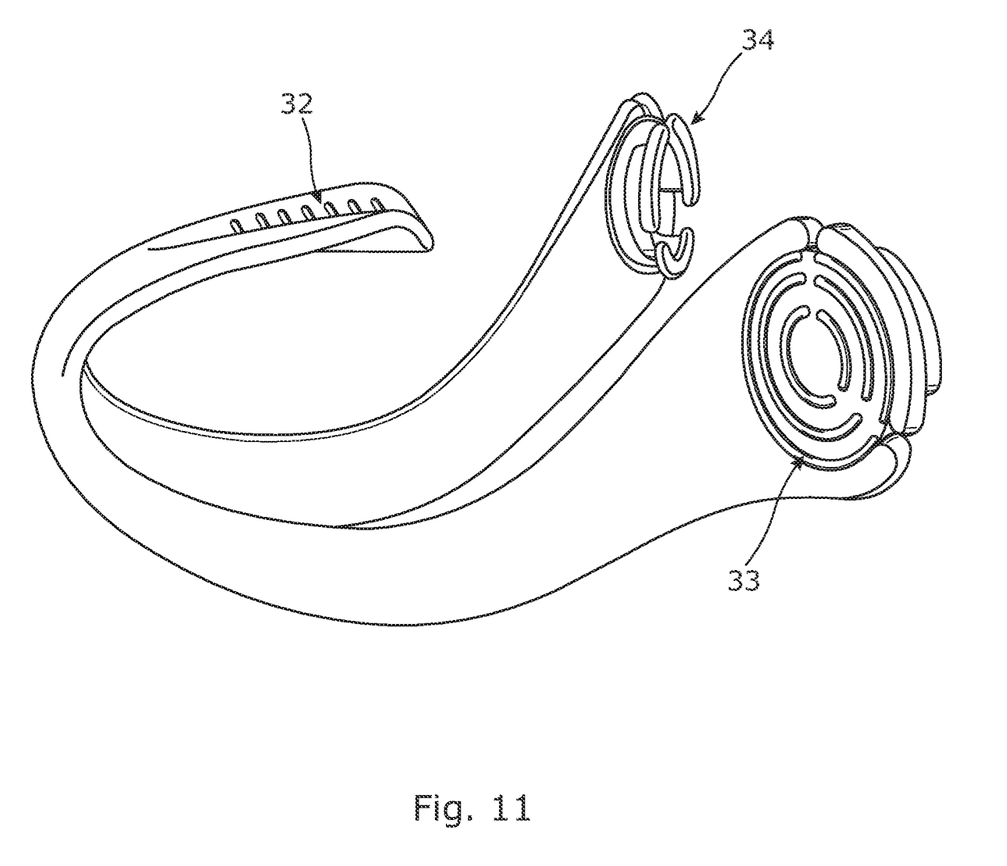
FIG. 11 is a side view of another embodiment of the vaginal assembly of the vaginal speculum according to the present invention, showing projections and slits on the separating elements for holding and/or securing suture materials and ridges on the separating elements for grasping and compressing the speculum on insertion and removal.

For example, the anterior wall element may comprise a depressed area 32 as illustrated in FIG. 11, configured to be grasped by the finger of a user. Further advantageously, the depressed area, or the depression, is placed centrally within the anterior wall element, such that when the assembly is grasped by the user for insertion or removal, the grasp generates a symmetrical distribution of the grasping force.

The depressed area may further comprise a surface profile or surface roughness, such as a corrugated or ridged surface as shown in FIG. 11 for further facilitating and simplifying the grasp.

In an embodiment of the disclosure, the anterior vaginal wall element comprises a depression adapted to be grasped by the user on insertion and removal. In a further embodiment, the depression is placed centrally within the anterior wall element. In a further embodiment, the anterior vaginal wall element comprises a surface profile adapted to be grasped by the user on insertion and removal.

For example, in some embodiments with an anterior vaginal wall element, a depression is included in the center of the flattened and rounded tongue shape of the anterior wall element. This depression enables the user to grasp the anterior vaginal wall element with a finger, which can be used to press the anterior vaginal wall element downwards for easier insertion and removal. The anterior vaginal wall element may be ridged to simplify grasping for insertion and removal.

Advantageously, one or both of the proximal ends of the separating elements comprises areas adapted to be grasped with one or more fingers. For example, a portion of the proximal ends of both the separating elements may comprise a surface profile or a surface roughness 33, as illustrated in FIG. 11, adapted to be grasped by the user. Further advantageously, when both ends comprises a surface profile, the vaginal assembly is further easily laterally compressed by two or more fingers from a single hand, such that the compression may be directed towards the centroid or geometric center of the assembly.

In some embodiments the separating elements of the vaginal assembly are ridged to simplify grasping by the user on insertion and removal. The surface profile may comprise ridges, optionally forming one or more concentric circular ridges, or parts of circular ridges, such that they are further adapted to be grasped with a finger, as shown in FIG. 11. Thus, the surface profile of the proximal ends of the separating elements facilitate easy, simple and safe insertion and removal, since the vaginal assembly is easier to grasp and/or compress by the user.

In an embodiment of the disclosure, the proximal ends of the separating elements comprises a surface profile adapted to be grasped by the user on insertion and removal. Advantageously, the vaginal speculum according to the present disclosure may further facilitate the suturing and/or examination process by e.g. facilitating the handling of suture materials or examination devices. For example, the proximal end of one or both separating elements may comprise protrusions, projections, and/or slits for holding and/or securing the materials used for suturing or examination. For example a protrusion or projection 34 may comprise one or more slits, as illustrated in FIG. 11. The protrusion is advantageously adapted to be used for holding a suture material, such as a thread, and the slit is advantageously adapted to be used for securing or fixing a suture material, such as a thread. For example, a thread may be placed over the projection and fastened to a slit in the same manner as a sewing thread to a bobbin. Thus, in some embodiments the proximal ends of one or both of the separating elements are provided with projections for holding materials for examination or suturing. In some embodiments the proximal ends of one or both of the separating elements are provided with slits for securely holding suture materials.

In an embodiment of the disclosure, at least one of the proximal ends of the separating elements comprises one or more projections for holding materials for examination or suturing. In another and further embodiment, at least one of the proximal ends of the separating elements comprises one or more slits for securing suture materials.

The material for the vaginal speculum should be chosen to match the desired properties for the speculum. In one embodiment the vaginal speculum is fabricated at least partially from an elastic material. In another embodiment the vaginal speculum is fabricated entirely from an elastic material. The vaginal speculum may in some embodiments be fabricated from metal or nylon or a plastic material such as polyethylene (PE), polypropylene (PP), polystyrene (PS) and polyvinyl chloride (PVC). Depending on the thickness and design of the speculum, these materials may be designed to provide more or less flexible properties. The speculum may also be fabricated from a combination of the listed materials. Manufacturing techniques that may be used for the vaginal speculum include injection molding and additive manufacturing.

In one embodiment at least part of the surface of the vaginal assembly is coated by a different material than the material of the vaginal assembly. In one example, the vaginal assembly is mainly fabricated from one material with elastic and/or resilient properties which is then at least partly coated in a second material for softness, smoothness, insulation or to make the assembly easier to handle or less traumatic for the patient. The coating may provide a smoother surface or reduced friction which also improves comfort and reduces trauma for the subject. At least part of the surface of the vaginal assembly may also be coated with a fluid or gel before or after packaging and before insertion into the vagina. This may be for lubricating and/or anesthetic purposes such that the speculum causes less discomfort during insertion and use.

In one embodiment of the present invention the speculum further comprises a soft padding material attachable or permanently attached to at least part the surfaces of the speculum. Again, this could provide better protection for the sensitive tissue, thereby improving comfort for the patient and cause the experience to be less traumatic. The padding material could be located at the proximal base elements and/or at the separating elements. For padding material at the separating elements, it is furthermore advantageous that the material is smooth, slippery and provides low friction against the tissue.

The vaginal speculum may furthermore comprise an absorbent material attachable or permanently attached to at least part the surfaces of the speculum. In one embodiment the absorbent material is attached or attachable to the inside of the separating elements. The inside of the separating elements refers to the part of the surface of the separating elements facing away from the vaginal tissue after the speculum is inserted into the vagina. This could act as an addition to or a replacement for a suction device. The absorbent material may be attached or attachable using an adhesive or by sliding the absorbent material into slots provided in the speculum. The absorbent material could also be mounted on another element that is secured to the inside of the separating element e.g. by sliding it into slots in the separating elements.

The vaginal speculum could be reusable by cleaning and sterilizing the speculum after use. Preferably the presently disclosed vaginal assembly or the entire speculum is disposable. Furthermore, the speculum is preferably sterilized and in a sealed package prior to use. This will lower the risk of infection after using the speculum. In one embodiment the vaginal assembly is configured to be resiliently elastic such that the vaginal assembly can be transversely compressed for insertion into the vagina. Prior to being inserted into the vagina, the vaginal assembly may thereby be compressed, by hand or using a tool. The vaginal assembly is then inserted into the vagina and the compression force is released such that the vaginal assembly transversely separates and holds the vaginal walls apart. In another embodiment the vaginal assembly is packaged in a compressed and compact condition for insertion into the vagina.

In some situations it may be advantageous and practical to attach other equipment to the speculum when performing examination, suturing or surgery on the subject. Therefore, the vaginal speculum is in one embodiment configured for attachment of additional equipment, such as one or more lights, or one or more cameras, or one or more suction tubes. In another embodiment the vaginal speculum further comprises one or more permanent or removable pads such as soft padding and/or fluid absorbent padding.

The third aspect of the invention relates to a method for providing an unobstructed view of at least the posterior part of the vaginal wall using a vaginal assembly and a locking element. In one embodiment the method further comprises the step of transversely compressing the vaginal assembly prior to insertion into the vagina. The speculum may be fabricated from at least a partly flexible material in which case the assembly should be transversely compressed for insertion into the vagina. In another embodiment the method further comprises the step of releasing the vaginal assembly from a compressed and compact configuration after insertion into the vagina. For a vaginal assembly fabricated from an elastic material, the assembly will then exert a transverse force on the vaginal walls and thereby separate and hold the vaginal walls apart such that at least the posterior part of the vagina is exposed. The method may furthermore be performed using the vaginal assembly and locking element according to the first aspect of the present invention.

However, the vaginal speculum is capable of exerting sufficient force on the vaginal walls for holding the walls apart without the use of a locking engagement. Therefore, in all embodiments it is envisaged that the speculum does not have engagement sections for engaging with a locking mechanism.

As detailed above, the vaginal speculum may comprise an anterior vaginal wall element which is connected at the distal end of the vaginal assembly and extending in the proximal direction from the distal end for supporting the anterior vaginal wall.

As with the longitudinal separating elements, the anterior vaginal wall element may also be fabricated from at least a partly flexible material. When the separating elements are transversely compressed for insertion into the vagina of a subject, the vaginal wall element may also be compressed towards the separating elements. The distal end of the speculum may then be advanced into the vagina of the subject in a position so that the anterior vaginal wall element is arranged to face the anterior wall of the vagina.

On being advanced to the desired depth within the vagina, the separating elements and vaginal wall element may be released so as to revert back from the compressed state towards their original non-compressed state. In doing so, the separating elements hold the lateral walls of the vagina apart and the anterior vaginal wall element supports and exerts pressure on the anterior wall of the vagina. As well as providing a supporting function, the anterior vaginal wall element may also act so as to rest behind the pubic bone of the subject when in the vagina and thus act as an anchor to retain the speculum in place when in use.

This configuration of the speculum comprising an anterior vaginal wall element has a particular advantage in providing a clearer and less obstructed view of the posterior section of the vagina, in particular the perineum, which is where the majority of tearing occurs during child birth.

DETAILED DESCRIPTION OF THE DRAWINGS

Figure 1:
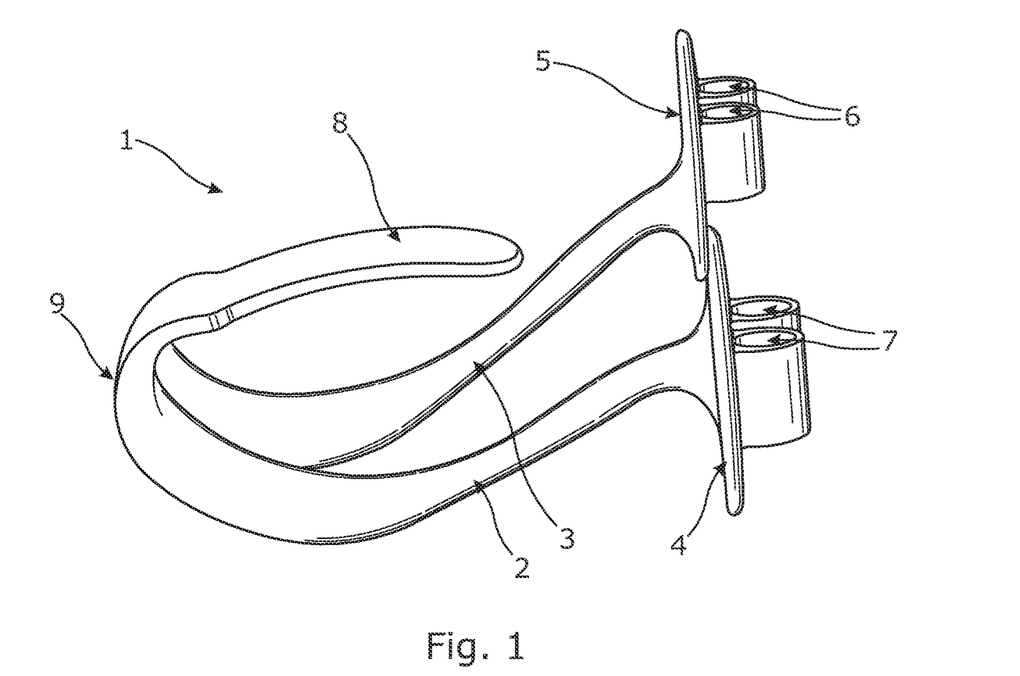
FIG. 1 is a side view of one embodiment of the vaginal assembly of the vaginal speculum according to the present invention.

FIG. 1 shows one embodiment of the vaginal assembly of the vaginal speculum according to the present invention. In this embodiment the speculum consists of two pieces, a vaginal assembly 1 and a locking element (not shown in this figure). The vaginal assembly 1 comprises two longitudinal separating elements 2,3 and each with a proximal base element 4,5 with engagement sections 6,7 for engaging the locking element with the vaginal assembly. The longitudinal separating elements 2,3 are connected at the distal tip 9. In this embodiment the vaginal assembly further comprises an anterior vaginal wall element 8 for supporting the anterior vaginal wall.

Figure 2:
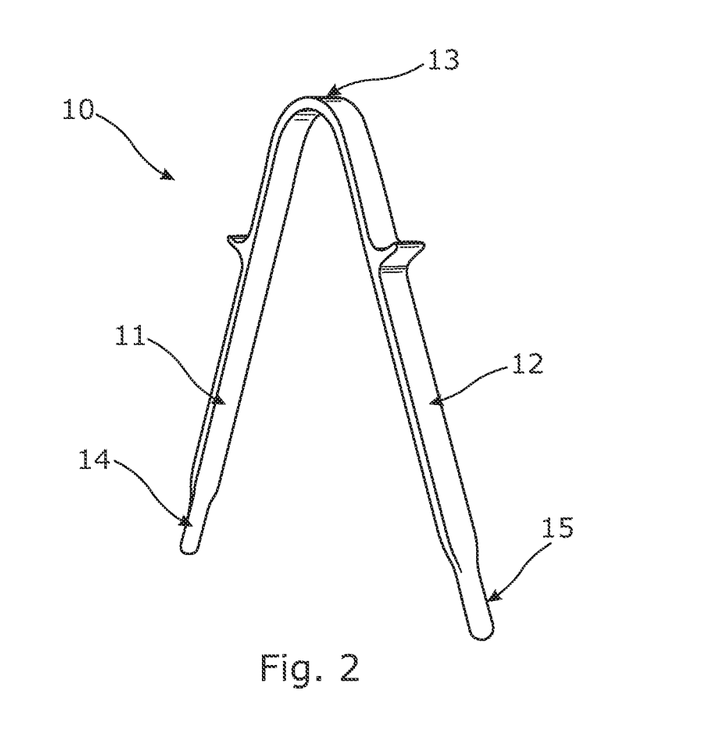
FIG. 2 shows one embodiment of the locking element used for the vaginal speculum in the present invention.

FIG. 2 illustrates one embodiment of a locking element 10 for use with the vaginal assembly in FIG. 1. The locking element consists of two arms 11,12 connected at one end 13 such that they are in the shape of an inverted V. The other ends 14,15 of the arms are configured for engagement with the vaginal assembly.

Figure 3:
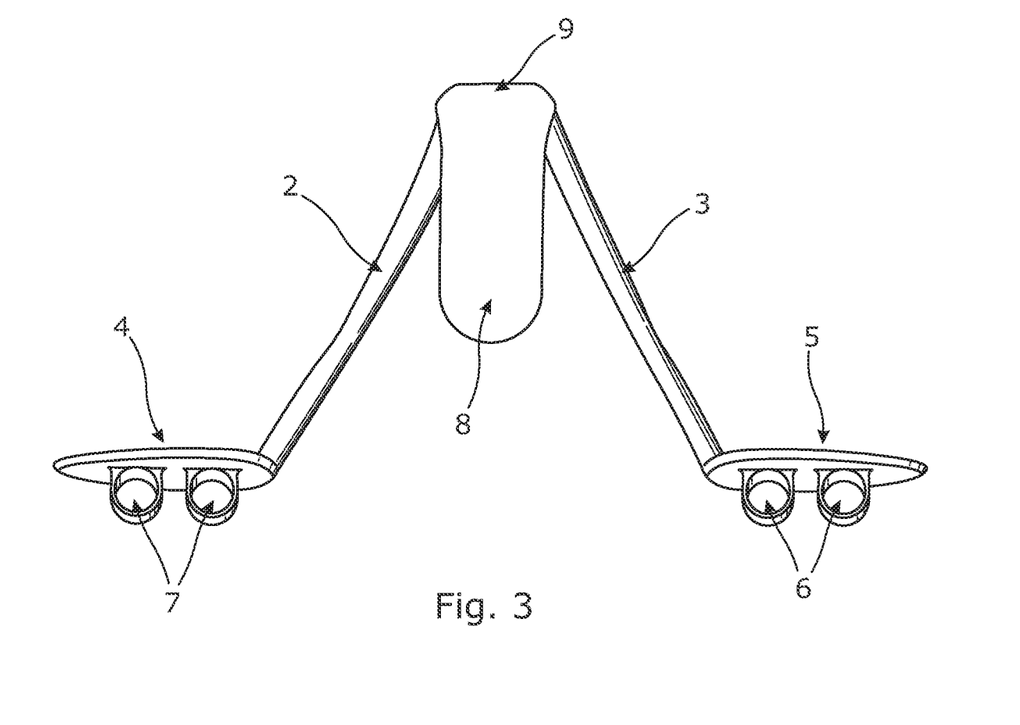
FIG. 3 is a top view of the vaginal assembly shown in FIG. 1.

FIG. 3 shows a top view of the vaginal assembly in FIG. 1. This view shows that the separating elements 2,3 are further apart at the proximal end than at the distal end. The material for the vaginal assembly may be flexible such that the assembly can be transversely compressed to a compact state before insertion into the vagina. The separating elements 2,3 may then at least partly separate and hold the vaginal walls apart when the compression force is released.

Figure 4:
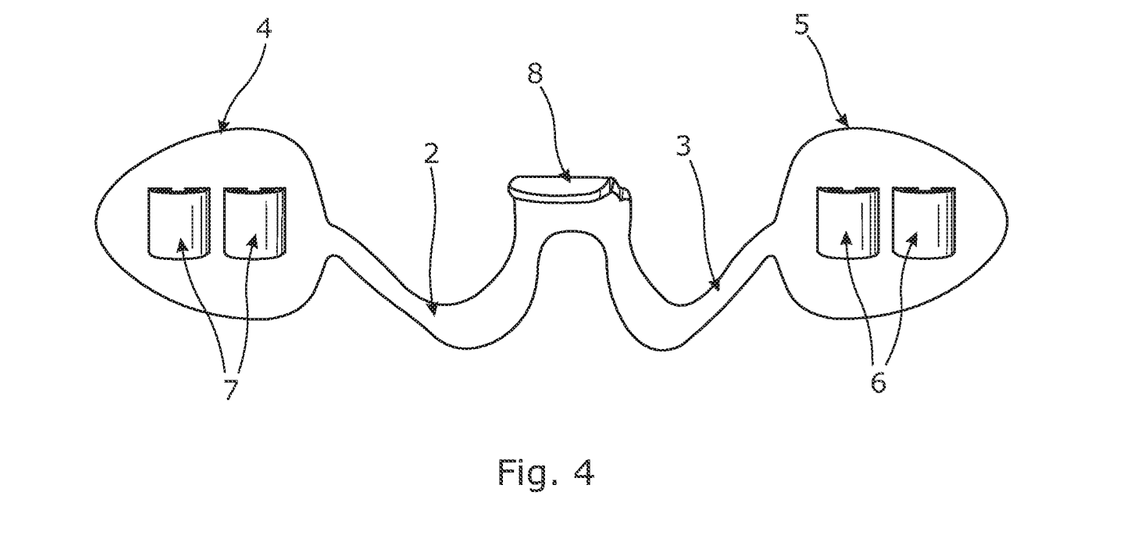
FIG. 4 is a front view, i.e. a view of the proximal end (from the user's perspective), of the vaginal assembly shown in FIGS. 1 and 3.

FIG. 4 is a front view, i.e. a view of the proximal end (from the user's perspective), of the vaginal assembly shown in FIGS. 1 and 3. The vaginal assembly 1 in this embodiment comprises two engagement sections 6,7 at each base element 4,5 such that the separation force can be adjusted by engaging the locking element with different engagement sections.

Figure 5:
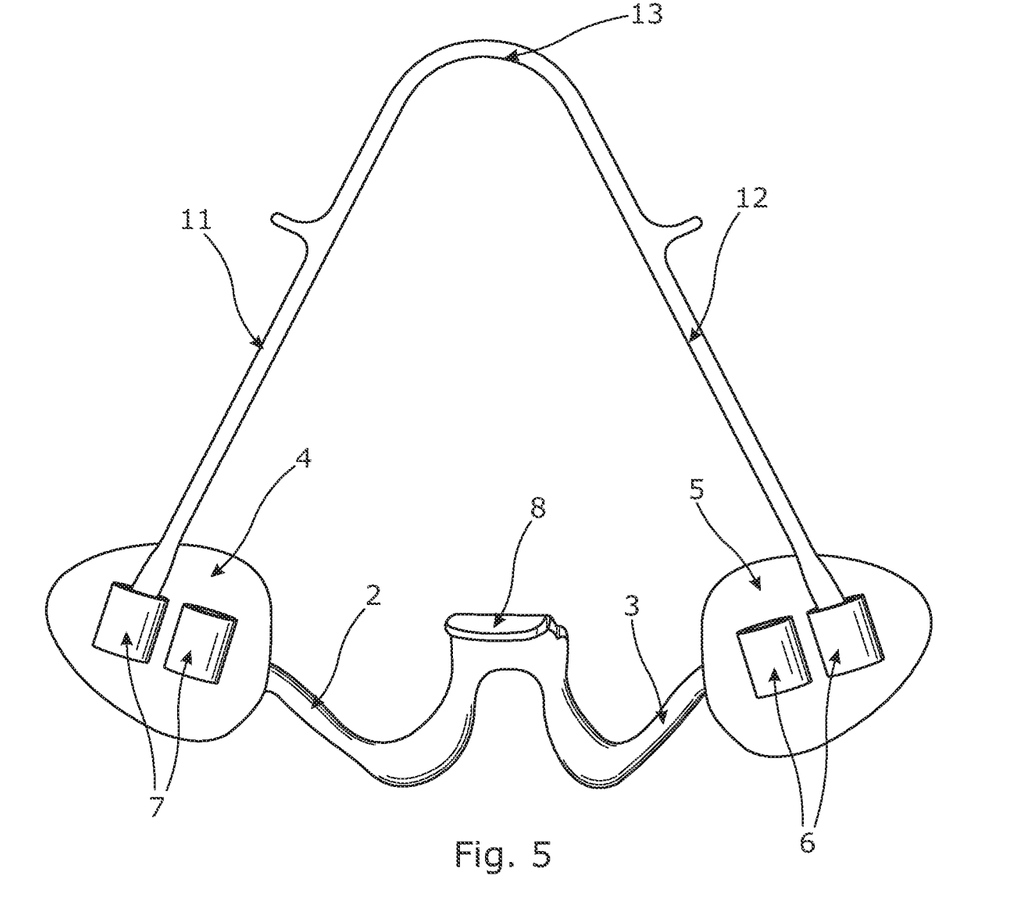
FIG. 5 shows a front view of the vaginal assembly shown in FIGS. 1, 3 and 4 with the locking element engaged with the vaginal assembly.

FIG. 5 shows a front view of the vaginal assembly shown in FIGS. 1, 3 and 4 with the locking element in FIG. 2 engaged with the vaginal assembly. The ends 14,15 of the locking element 10 are engaged with the engagement sections 6,7 of the vaginal assembly such that a transverse separation force is exerted by the locking element on the vaginal assembly.

Figure 6:
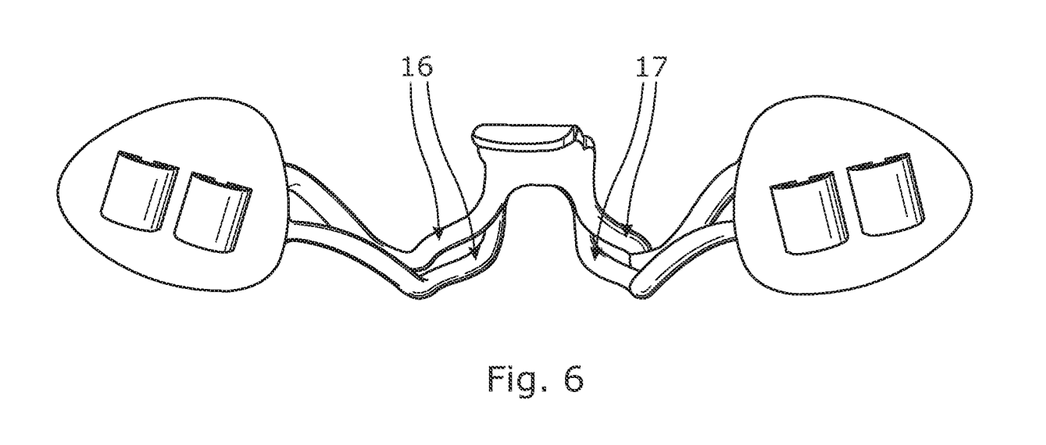
FIG. 6 is a front view of a second embodiment of the vaginal assembly of the vaginal speculum according to the present invention.

FIG. 6 is another embodiment of the vaginal assembly. This embodiment comprises two separation elements for each side such that a total of four separation elements are connected at the distal end. The two left separation elements 16 are connected to a base element on the left side and correspondingly the two right separation elements 17 are connected to a base element on the right side. Vaginal assemblies with multiple separation elements may in some cases be advantageous and provide less discomfort for the subject. Furthermore, the separating elements are shaped such that they provide additional separating pressure. The separating elements initially extend in a proximal direction from the distal tip end. The left and right separating elements then curve away from each other such that the distance between them becomes larger and then curve back to become parallel or almost parallel. Finally, the separating elements curve such that the distance between them increases at the proximal end where the base elements are connected. This design of the speculum provides additional separating force the areas where the distance between the separating elements is large which may be advantageous for providing a clear and unobstructed view.

Figure 7:
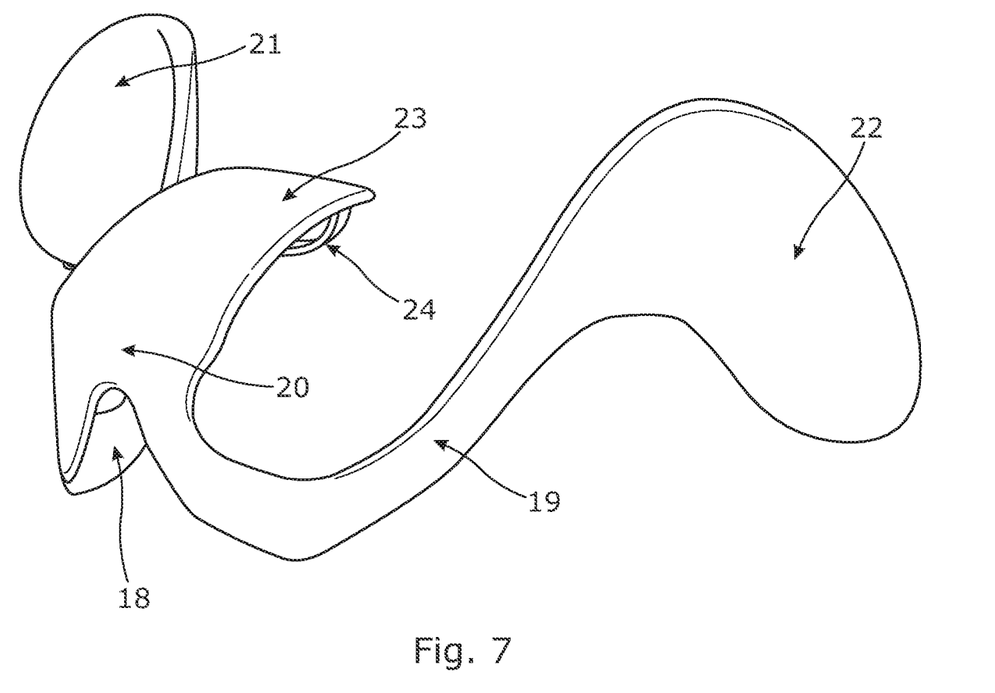
FIG. 7 is an oblique view of a third embodiment of the vaginal assembly of the vaginal speculum according to the present invention.

FIG. 7 shows yet another embodiment of the vaginal assembly comprising two longitudinal separating elements 18,19 connected at the distal tip 20 end and each with a proximal base element 21,22. The vaginal assembly further comprises an anterior vaginal wall element 23 for supporting the anterior vaginal wall. A grip 24 is provided on the anterior vaginal wall element for pulling the anterior vaginal wall element downward for ease of insertion and removal of the vaginal assembly.

Figure 8:
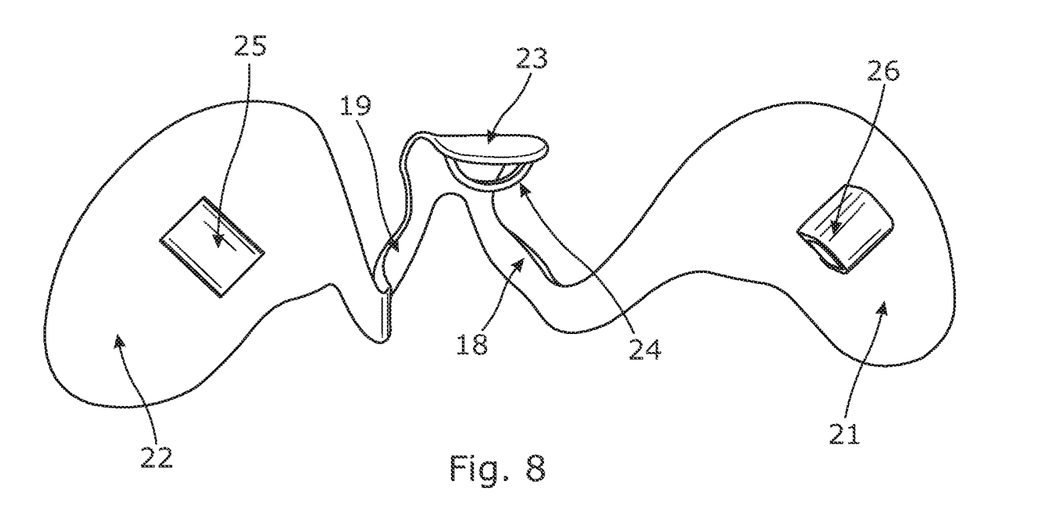
FIG. 8 is a front view of the vaginal assembly shown in FIG. 7.

FIG. 8 is a front view of the vaginal assembly in FIG. 7. The figure shows an engagement section 25,26 on each of the base elements 21,22 for engagement with a locking element. The shape of the separating elements is similar to the ones in FIG. 6 such that the speculum provides additional separating force in areas where the separating elements are separated by a large distance.

Figure 9:
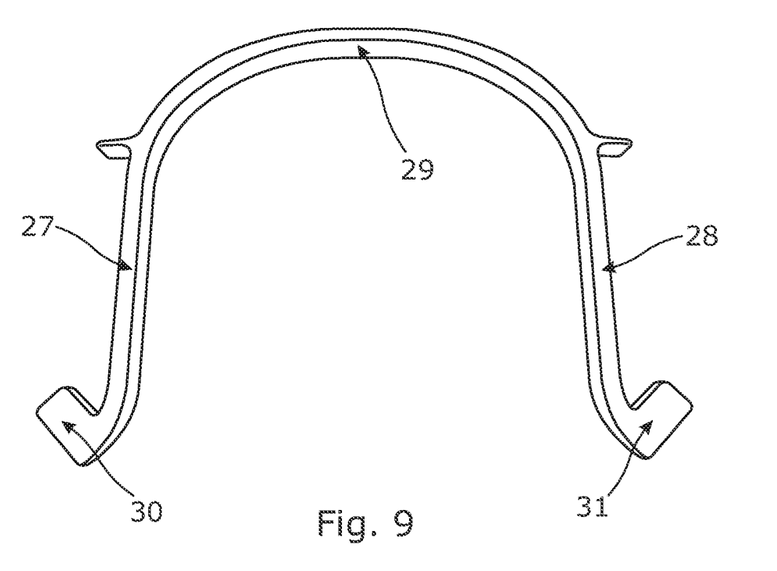
FIG. 9 shows another embodiment of the locking element that may be used with the vaginal assembly in FIGS. 7 and 8.

FIG. 9 shows an embodiment of a locking element for use with the vaginal assembly shown in FIGS. 7 and 8. This embodiment of the locking element is in the shape of an arch or an inverted U and comprises two side elements 27,28 connected at the top by a center element 29. Each bottom end 30,31 of the side arms is configured for engagement with the engagement sections on the vaginal assembly.

Figure 10:
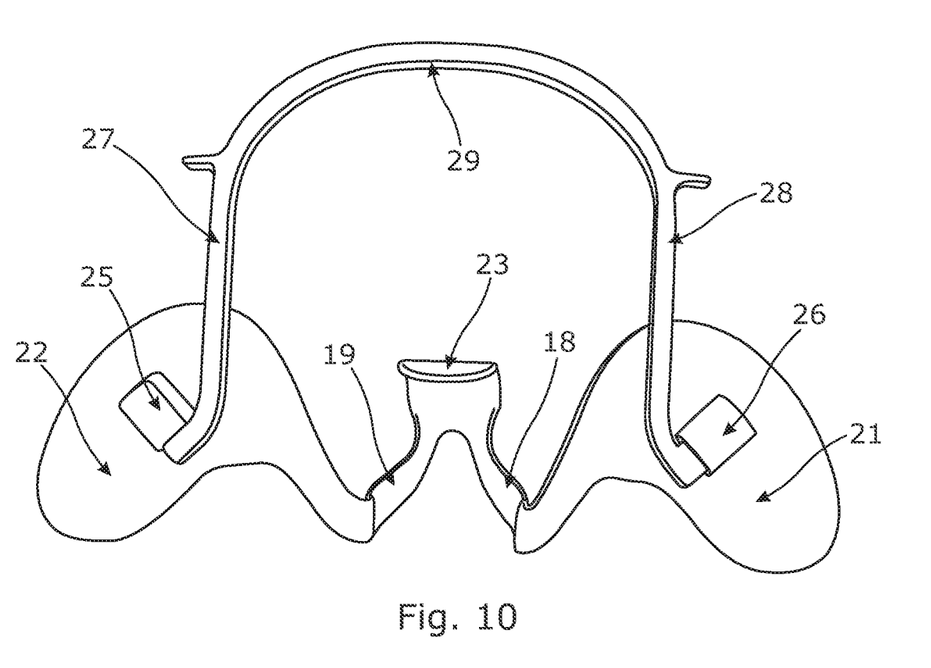
FIG. 10 is a front view of the vaginal assembly shown in FIGS. 7 and 8, with the locking element engaged with the vaginal assembly.

FIG. 10 shows the locking element in FIG. 9 engaged with the vaginal assembly shown in FIGS. 7 and 8. The locking element engages with the engagement sections on the vaginal assembly at an angle such that the locking element is safely engaged with the vaginal assembly with a low risk of disengagement during use of the speculum. The figure also shows the shape of the separating elements as described for FIG. 8 for providing additional separating force.

FIG. 11 shows an embodiment of the vaginal assembly, where the assembly is configured to assume the desired shape on insertion, by tailoring the materials and dimensions of the assembly. The vaginal assembly is shown in a side view, and comprises multiple areas adapted to be grasped by one or more fingers. The anterior wall element comprises a depressed and ridged area 32 placed centrally in the anterior wall element, and the proximal ends of the separating elements comprised concentric circular ridges 33 adapted to be grasped with one or more fingers. Preferably the areas adapted to be grasped are grasped by the fingers of a single hand, such that the assembly is easily handled and compressed, thereby facilitating the insertion and removal of the speculum. The compression may be directed towards the centroid or geometric center of the assembly, thereby facilitating the insertion and removal of the speculum. The embodied assembly further comprises projections and slits 34 on proximal ends of the separating elements for holding and/or securing suture materials.

Figure 12:
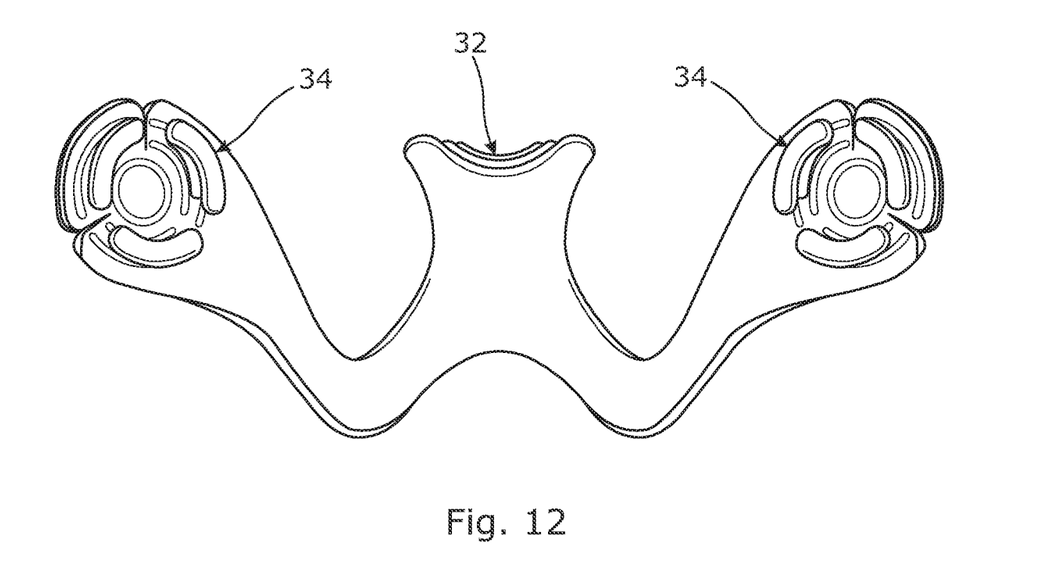
FIG. 12 is a front view of the vaginal assembly shown in FIG. 11, where a depression is provided in the anterior vaginal wall element for grasping and compressing the speculum on insertion and removal.

FIG. 12 is a front view of the vaginal assembly shown in FIG. 11, where a depression is provided in the anterior vaginal wall element for grasping and compressing the speculum on insertion and removal.

Figure 13:
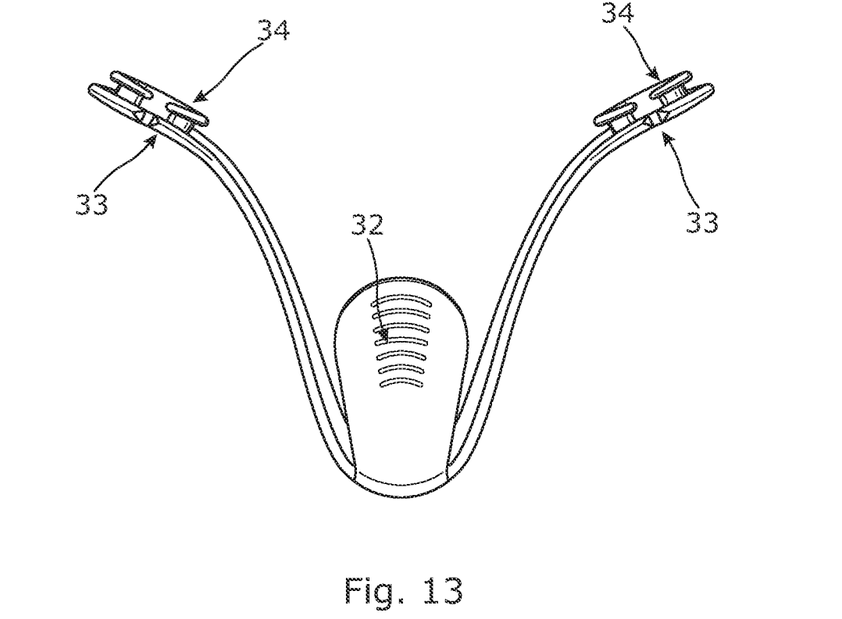
FIG. 13 is a top view of the vaginal assembly shown in FIGS. 11 and 12, with ridges on the anterior vaginal wall element for grasping and compressing the speculum on insertion and removal.

FIG. 13 is a top view of the vaginal assembly shown in FIGS. 11 and 12, with ridges on the anterior vaginal wall element for grasping and compressing the speculum on insertion and removal.

I claim:

1. A vaginal assembly comprising:
   at least two longitudinal separating elements directly connected to each other at a distal end of each of the at least two longitudinal separating elements configured for insertion into a vagina of a subject,
   wherein the vaginal assembly is configured for holding vaginal walls of the subject apart, thereby permitting examination and suturing of at least a posterior part of vaginal tissue of the vagina;
   wherein the vaginal assembly further comprises an anterior vaginal wall element configured for supporting an anterior vaginal wall and configured to rest behind a pubic bone of the subject when in the vagina and thereby act as an anchor to retain the assembly in place when in use;
   wherein the vaginal assembly further comprises a proximal base element located at a proximal end of each of the at least two longitudinal separating elements;
   wherein each proximal base element curves outwards from the respective longitudinal separating element on which it is located such that the proximal base elements are configured to rest on a skin outside the vagina after the vaginal assembly has been inserted in the vagina of the subject;
   wherein each proximal base element comprises a protrusion, projection, or slit configured for holding or securing a material used for examination and suturing; and
   wherein the anterior vaginal wall element is shorter than the at least two longitudinal separating elements.

2. The vaginal assembly according to claim 1, wherein the anterior vaginal wall element is connected at a distal end of the vaginal assembly, extending in a proximal direction from the distal end of the vaginal assembly.

3. The vaginal assembly according to claim 1, wherein the anterior vaginal wall element is in a shape of a tongue including a flattened and rounded shape.

4. The vaginal assembly according to claim 1, wherein the anterior vaginal wall element is made from an elastic material such that it is configured to support the anterior vaginal wall.

5. The vaginal assembly according to claim 1, wherein the proximal base elements are configured for resting against, separating, and holding apart the labia majora and labia minora.

6. The vaginal assembly according to claim 1, wherein the vaginal assembly is configured for supporting the anterior vaginal wall of the subject on which pressure is exerted by a bladder.

7. The vaginal assembly according to claim 1, wherein the vaginal assembly is fabricated at least partially from an elastic material.

8. The vaginal assembly according to claim 1, wherein the vaginal assembly is fabricated entirely from an elastic material.

9. The vaginal assembly according to claim 1, wherein the vaginal assembly is fabricated from metal, nylon, a plastic material, or any combination thereof.

10. The vaginal assembly according to claim 1, wherein the assembly is sterilized and in a sealed package prior to use.

11. The vaginal assembly according to claim 1, configured to be resiliently elastic such that the vaginal assembly can be transversely compressed for insertion into the vagina.

12. A kit-of-parts comprising a vaginal assembly according to claim 1 in a form of a sterile, pre-packaged kit-of-parts for single use.

13. A method for inserting a vaginal assembly into a vagina of a subject, wherein the method comprises the steps of providing a vaginal assembly according to claim 1 and inserting a distal end of the assembly into the vagina of the subject.

14. The method according to claim 13 wherein prior to insertion the at least two longitudinal separating elements are transversely compressed towards each other from a resting state to a compressed state.

15. The method according to claim 14 wherein after insertion the at least two longitudinal separating elements are released and return from the compressed state to the resting state.

16. The vaginal assembly according to claim 1, wherein the anterior vaginal wall element is configured to be compressed towards the at least two longitudinal separating elements during insertion of the vaginal assembly into the vagina of the subject and is configured to revert back to an original non-compressed state configured for supporting the anterior vaginal wall after the vaginal assembly is advanced to a desired depth within the vagina of the subject.

17. The vaginal assembly according to claim 1, wherein the vaginal assembly is a vaginal speculum.

\* \* \* \* \*